United States Patent [19]
Kato et al.

[11] Patent Number: 5,824,527
[45] Date of Patent: Oct. 20, 1998

[54] FRUCTOSYL AMINO ACID OXIDASE AND PROCESS FOR PRODUCING THE SAME

[75] Inventors: Nobuo Kato, Kameoka; Yasuyoshi Sakai, Otsu; Yoshiki Tani; Masayuki Yagi, both of Kyoto; Fumiyo Funatsu, Hirakata, all of Japan

[73] Assignee: Kyoto Daiichi Kagaku Co., Ltd., Kyoto-fu, Japan

[21] Appl. No.: 630,175

[22] Filed: Apr. 11, 1996

[30] Foreign Application Priority Data

Apr. 11, 1995 [JP] Japan .................................. 7-085261

[51] Int. Cl.$^6$ .............................. C12N 9/06; C12N 9/02; C12Q 1/26
[52] U.S. Cl. ........................... 435/191; 435/189; 435/25; 435/28; 435/72; 435/105; 435/106
[58] Field of Search .................................... 435/189, 191, 435/25, 28, 72, 105, 106

[56] References Cited

U.S. PATENT DOCUMENTS 5,387,109  2/1995  Ishikawa et al. ........................ 435/191

FOREIGN PATENT DOCUMENTS 0 678 576 A2  10/1995  European Pat. Off. .
0 709 457 A1   5/1996  European Pat. Off. .
   0044874      1/1992  Japan .

OTHER PUBLICATIONS

Watanabe et al, Agric. Biol. Chem. 54(4): 1063–1064 (1990).
Yoshida et al., Applied and Environmental Microbiology, "Distribution and Properties of Fructosyl Amino Acid Oxidase in Fungi", vol. 61, No. 12, Dec. 1995, pp. 4487–4489.
Horiuchi et al., Agricultural and Biological Chemistry, "Purification and Properties of Fructosyl–amino Acid Oxidase from *Coryne bacterium* Sp. 2–4–1", vol. 53, No. 1, 1989, pp. 103–110.

*Primary Examiner*—Francisco C. Prats
*Attorney, Agent, or Firm*—Birch, Stewart, Kolasch & Birch, LLP

[57] ABSTRACT

A novel fructosyl amino acid oxidase derived from genus Penicillium, which is active on both of fructosyl lysine and fructosyl valine, a process for producing the enzyme, an assay of an amadori compound using the enzyme, a reagent or a kit containing the enzyme is provided.

7 Claims, 9 Drawing Sheets

A : Molecular weight Marker
B : Purified FAOD

FRUCTOSYL AMINO ACID OXIDASE AND PROCESS FOR PRODUCING THE SAME

FIELD OF THE INVENTION

The present invention relates to a novel fructosyl amino acid oxidase. More particularly, it relates to a novel fructosyl amino acid oxidase derived from genus Penicillium, a process for producing the enzyme, an assay of an amadori compound using the enzyme, and a reagent or a kit containing the enzyme.

BACKGROUND OF THE INVENTION

When reactive substances such as proteins, peptides and amino acids having an amino group(s) coexist with a reducing sugar such as aldose having an aldehyde group(s), they combine nonenzymatically and irreversibly through the amino and aldehyde groups, which is followed by amadori rearrangement to form an amadori compound. The production rate of an amadori compound being a function of concentration of reactants, period of contact, temperature and the like, determination of amadori compounds in a sample provides various useful information about the sample. Examples of materials generally containing an amadori compound include food products such as soy sauce and body fluids such as blood.

In a living body, fructosylamines are formed through the glycation reaction between glucose and various amino acids. For example, glycation products of hemoglobin and albumin in blood are called glycohemoglobin and glycoalbumin, respectively. The term "fructosamine" is referred to the ability of fructosylamines to act as reducing agents in alkaline solution. As the concentration of these glycated derivatives in blood should reflect an average of blood sugar levels over a particular period of time, it can be used as a significant index for diagnosis and control of conditions of diabetes. Therefore, the establishment of a method of measuring an amadori compound in blood is clinically useful.

Further, a state of preservation and period after production of a food product can be estimated on the basis of the amount of amadori compounds in the food product. Therefore, the method of measuring an amadori compound can also contribute to the quality control of a food product.

As exemplified above, an assay of amadori compounds should be useful in a wide range of fields involving medicine and food products.

Examples of assay of amadori compounds include a method which utilizes high performance liquid chromatography [Chromatogr. Sci. 10:659 (1979)], a column filled with solid materials to which boric acid is attached [Clin. Chem. 28:2088–2094 (1982)], electrophoresis [Clin. Chem. 26:1598–1602 (1980)] or antigen-antibody reaction [JJCLA 18:620 (1993), J. Clin. Lab. Inst. Reag. 16:33–37 (1993)], a method for measuring the amount of fructosamine [Clin. Chim. Acta 127:87–95 (1982)], a calorimetric determination following the oxidization with thiobarbituric acid [Clin. Chim. Acta 112:197–204 (1981)], or the like. These existing methods, however, require an expensive device(s) and are not necessarily accurate and rapid enough.

In the field of clinical assay and food analysis, a method utilizing enzymatic process has become more and more popular, because, owing to characteristics of enzymes (specificity in terms of substrate, reaction, structure, active site, etc.), an intended substance can be selectively analyzed with accuracy and rapidity.

There have been provided assays which comprise reacting an oxidoreductase with amadori compounds and determining oxygen consumption or hydrogen peroxide generation as an index of the amount of amadori compounds (e.g. Japanese Patent Publication (KOKOKU) Nos. 5-33997 and 6-65300, and Japanese Laid-Open Patent Publication Nos. 2-195900, 3-155780, 4-4874, 5-192193, 6-46846 and 7-289253). Further, assays of glycated protein for the diagnosis of diabetes have also been proposed (Japanese Laid-Open Patent Publication Nos. 2-195899, 2-195900, 5-192193, 6-46846 and 7-289253).

The decomposition of amadori compounds catalyzed by an oxidoreductase can be represented by the following reaction scheme:

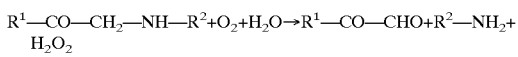

wherein $R^1$ is an aldose residue and $R^2$ is an amino acid, protein or peptide residue.

Examples of enzymes which catalyze the above reaction are as follows:

1. fructosyl amino acid oxidase derived from Corynebacterium (Japanese Patent Publication Nos. 5-33997 and 6-65300) or Aspergillus (Japanese Laid-Open Patent Publication No. 3-155780)];
2. fructosylamine deglycase derived from Candida (Japanese Laid-Open Patent Publication No. 6-46846);
3. fructosyl amino acid deglycase derived from Penicillium (Japanese Laid-Open Patent Publication No. 4-4874);
4. ketoamine oxidase derived from Corynebacterium, Fusarium, Acremonium or Debaryomyces (Japanese Laid-Open Patent Publication No. 5-192193)]; and
5. alkyllysinase which can be prepared according to the method described in J. Biol. Chem., Vol. 239, pp. 3790–3796 (1964).

Assays involving these existing enzymes, however, have drawbacks.

For instance, indexes for the diagnosis of diabetes in blood are glycated albumin, glycated hemoglobin and fructosamine. Glycated albumin is formed when glucose is bound to a lysine residue at its ε-position on protein molecule [J. Biol. Chem., 261:13542–13545 (1986)]. In the case of glycated hemoglobin, glucose is also bound to N-terminal valine of β-chain [J. Biol. Chem. 254:3892–3898 (1979)]. Therefore, it is necessary to use an enzyme highly specific to fructosyl valine as well as to fructosyl lysine to conduct the determination of glycated proteins as an index of diabetes efficiently. However, an enzyme derived from Corynebacterium does not act on fructosyl lysine. As for an enzyme from Aspergillus, its action on glycated proteins or hydrolyzed products thereof is unclear. Although the ketoamine oxidase described in Japanese Laid-Open Patent Publication No. 5-192193 reacts on fructosyl valine, it does not afford an accurate assay of glycated proteins where a lysine residue is bound to a sugar. Because the fructosylamine deglycase is highly specific to difructosyl lysine, it cannot afford an assay specific to a substance in which a lysine residue is glycated at the ε-position or a valine residue is glycated. Furthermore, a method using an alkyllysinase cannot be reliable or accurate because said enzyme lacks in specificity and reacts with substances even if lysine residue is bonded to a moiety other than sugar. Fructosyl amino acid deglycase derived from Penicillium (Japanese Laid-Open Patent Publication No. 4-4874) reacts on both of fructosyl lysine and fructosyl alanine.

As described above, existing enzymes cannot necessarily give an accurate assay of glycated proteins and therefore the development of an enzyme highly specific to fructosyl lysine and fructosyl valine has been demanded.

In general, for the improvement of accuracy and usefulness of an assay involving an enzymatic process, it is essential to use an enzyme having a catalytic activity suitable for purposes of a given assay. Thus, it is necessary to select an appropriate enzyme taking many factors such as the substance (i.e., substrate) to be determined, the condition of the sample, measuring conditions and the like into consideration in order to carry out the assay with accuracy and reproducibility. For such a purpose, one must previously obtain many enzymes and clarify their activity, substrate specificity, temperature stability, pH stability and the like. Therefore, it is necessary to develop more and more fructosyl amino acid oxidases and characterize the same.

SUMMARY OF THE INVENTION

The present inventors have intensively studied for purposes of providing a novel fructosyl amino acid oxidase specific to amadori compounds, particularly to glycated protein, and have found that objective enzymes can be obtained by culturing a strain of Penicillium in the presence of fructosyl lysine and/or fructosyl $N^\alpha$-Z-lysine.

Thus, the present invention provides a novel fructosyl amino acid oxidase, which is produced by culturing a strain of Penicillium capable of producing a fructosyl amino acid oxidase in a medium containing fructosyl lysine and/or fructosyl $N^\alpha$-Z-lysine.

DETAILED DESCRIPTION OF THE INVENTION

For purposes of the present invention, a medium containing fructosyl lysine contains fructosyl lysine and/or fructosyl $N^\alpha$-Z-lysine, which is used for culturing a microorganism capable of producing a fructosyl amino acid oxidase of the present invention, comprises fructosyl lysine and/or fructosyl $N^\alpha$-Z-lysine (hereinafter, it may be abbreviated as "FZL") obtained by autoclaving glucose together with lysine and/or $N^\alpha$-Z-lysine at 100° to 150° C. for 3 to 60 minutes. As is hereinafter described, the fructosyl amino acid oxidase of the present invention is unexpectedly specific to both of fructosyl valine and lysine, and it is characteristically more active on the former. Throughout the specification, the term "fructosyl amino acid oxidase" of the present invention may be abbreviated as "FAOD".

The enzyme of the present invention can be prepared by culturing a strain of Penicillium capable of producing FAOD in a medium containing fructosyl lysine and/or FZL.

Examples of strains of Penicillium include *Penicillium janthinellum* S-3413 (FERM BP-5475), *Penicillium janthinellum* (IFO No. 4651, 6581, 7905), *Penicillium oxalicum* (IFO No. 5748), *Penicillium javanicum* (IFO No. 7994), *Penicillium chrysogenum* (IFO No. 4897) and *Penicillium cyaneum* (IFO No. 5337).

FAODs of the present invention generally have the following physicochemical characteristics:

1) they catalyze the oxidation of an amadori compound in the presence of oxygen to generate α-ketoaldehyde, amine derivatives and hydrogen peroxide;
2) they are stable in the pH range of about 4.0 to 11.0 with an optimal pH of 7.5;
3) they are stable in the temperature range of about 15° to 50° C. with an optimal temperature of 25° C.; and
4) the molecular weight is about 38,700 (38.7 kDa) when estimated by gel filtration with Superdex 200 pg.

Fructosyl lysine and/or FZL used for the preparation of FAOD of the present invention can be obtained by autoclaving 0.01 to 50% (w/w) glucose together with 0.01 to 20% (w/w) lysine and/or $N^\alpha$-Z-lysine in a solution at 100° to 150° C. for 3 to 60 minutes. Specifically, it is prepared by autoclaving a solution containing, in a total volume of 1000 ml, 200 g of glucose and 10 g of $N^\alpha$-Z-lysine at 120° C. for 20 minutes.

A medium containing fructosyl lysine and/or FZL (hereinafter, referred to as FZL medium) is obtainable by adding fructosyl lysine and/or FZL obtained in a manner described above to any one of conventional media, but it can be conveniently prepared by autoclaving a mixture (preferably, pH 5.6 to 6.0) comprising 0.01 to 50% (w/w) glucose, 0.01 to 20% (w/w) lysine and/or $N^\alpha$-Z-lysine, 0.1% (w/w) $K_2HPO_4$, 0.1% (w/w) $NaH_2PO_4$, 0.05% (w/w) $MgSO_4.7H_2O$, 0.01% (w/w) $CaCl_2.2H_2O$ and 0.2% (w/w) yeast extract at 100° to 150° C. for 3 to 60 minutes.

The medium usable for the production of FAOD of the present invention can be a synthetic or natural medium which is generally used in the art and contains a carbon source, nitrogen source, inorganic substance and other nutrients. Examples of carbon source include glucose, xylose, glycerin and the like; examples of nitrogen source include peptone, casein digest, yeast extract, and the like; and examples of inorganic substance include sodium, potassium, calcium, manganese, magnesium, cobalt, and the like which are usually contained in a normal medium.

FAOD of the present invention can be induced to the highest extent when a microorganism capable of producing the same is cultured in a medium containing fructosyl lysine and/or FZL. Examples of preferred medium include fructosyl lysine- and/or FZL-containing medium (1.0% glucose, 0.5% fructosyl lysine and/or FZL, 1.0% $K_2HPO_4$, 0.1% $NaH_2PO_4$, 0.05% $MgSO_4.7H_2O$, 0.01% $CaCl_2.2H_2O$ and 0.01% vitamin mixture), in which fructosyl lysine and/or FZL is used as the sole nitrogen source and glucose as the carbon source.

A medium (pH 5.6 to 6.0) containing 20 g (2%) of glucose, 10 g (1%) of fructosyl lysine and/or FZL, 1.0 g (0.1%) of $K_2HPO_4$, 1.0 g (0.1%) of $NaH_2PO_4$, 0.5 g (0.05%) of $MgSO_4.7H_2O$, 0.1 g (0.01%) of $CaCl_2.2H_2O$ and 2.0 g (0.2%) of yeast extract in 1,000 ml of a total volume is especially preferred.

The medium containing fructosyl lysine and/or FZL can be prepared by adding fructosyl lysine and/or FZL to any of conventional medium, or by autoclaving a medium containing glucose together with lysine and/or $N^\alpha$-Z-lysine. The medium obtained by either method is colored brown owing to the presence of fructosyl lysine and/or FZL and is therefore referred to as "FZL brown-colored medium or GL (glycated lysine and/or glycated $N^\alpha$-Z-lysine) brown-colored medium".

The cultivation is normally conducted at temperature range of 25° to 37° C., preferably at 28° C. in a medium of pH range of 4.0 to 8.0, preferably 5.5 to 6.0. However, the culturing conditions may vary depending on various factors such as conditions of microorganisms and should not be limited to those described above. For instance, *P. janthinellum* S-3414 strain, when cultured for 20 to 48 hours, preferably for 36 hours under these conditions, FAOD is accumulated in the culture medium (see, FIG. 1). The resultant culture medium is then treated in a conventional manner to remove nucleic acids, cell wall fragments and the like to yield an enzyme preparation.

Since the enzyme activity of FAODs of the present invention are normally accumulated in bacterial/fungal cells, cells in the culture are harvested and ground to extract the enzyme.

The grinding of cells can be carried out in a conventional manner, for example, by means of mechanical grinding, autodigestion with a solvent, freezing, ultrasonic treatment, pressurization, or the like.

The method of isolation and purification of an enzyme is also known in the art. It can be conducted by combining known methods such as salting-out with ammonium sulfate, precipitation with an organic solvent such as ethanol, etc., ion-exchange chromatography, hydrophobic chromatography, gel filtration, affinity chromatography, and the like.

For example, mycelia are harvested by subjecting the resultant culture to centrifugation or suction filtration, washed, suspended in 0.1M Tris-HCl buffer (pH 8.5), ground with Dino-Mill and centrifuged. The supernatant as cell-free extract is then purified using, for example, fractionation with ammonium sulfate and DEAE-Sephacel ion-exchanging chromatography.

For purposes of the present invention, FAOD includes any enzyme-containing substances and solutions obtainable throughout the total purification process irrespective of the purity of the enzyme, including the cultured medium as far as the substances and solutions have the ability to catalyze the oxidization of amadori compounds as defined above.

Further, any fragments of FAOD which are associated to the enzymatic activity of FAOD and maintain the same fall within the scope of the invention because such fragments are also useful for purposes of the present invention.

FAOD thus obtained is useful for determining amadori compounds, particularly, glycated proteins in the diagnosis of diabetes.

The present invention also provides a process for producing FAOD, which comprises culturing a strain of Penicillium capable of producing FAOD in a medium containing fructosyl lysine and/or fructosyl $N^{\alpha}$-Z-lysine and recovering FAOD from the resulting culture.

*P. janthinellum* S-3413 (hereinafter referred to as S-3413 strain), one of strains producing FAOD of the present invention, is a novel fungus which has been isolated from the soil by the present inventors. The classification of the isolated fungus was carried out in accordance with the teaching of Udagawa Shunichi et al., "KINRUI-ZUKAN" Kodan-sha Scientific, 1993. The mycological characteristics thereof are shown below.

(1) It does not form ascus generation.
(2) It forms penicillus.
(3) It has a pear-shaped phialide which is suddenly narrowed at its top to form a long fine tip.
(4) The penicillus is branched and spreads irregularly.
(5) It does not form sclerotium.
(6) The conidium linkage spreads markedly.
(7) The growing conditions in medium are as follows:
It grows rapidly in Czapek agar medium. When cultured in a thermostatic chamber at 25° C. for 10 days, strains spread like wool which is colored pale yellow or grayish green. Also observed are radial deep wrinkles.

The S-3413 strain had been originally deposited as a domestic microorganism deposit (FERM P-14867, deposition date: Mar. 14, 1994) at the "National Institute of Bioscience and Human-Technology, Agency of Industrial Science and Technology", Tsukuba-shi, Ibaraki-ken, Japan and converted into an international one (FERM BP-5475) under the Budapest Treaty on Mar. 14, 1996.

FAODs of the present invention have the following characteristics:

1. Normal induction characteristics FAOD of the present invention is an inducible enzyme induced by fructosyl lysine and/or FZL and is produced by culturing a strain of Penicillium capable of producing FAOD in a medium containing fructosyl lysine and/or FZL as the nitrogen source and glucose as the carbon source. FAOD can be induced in a GL brown-colored medium obtained by autoclaving glucose together with lysine and/or $N^{\alpha}$-Z-lysine but not in a medium containing glucose and lysine and/or $N^{\alpha}$-Z-lysine which have been autoclaved separately, which indicates that the enzyme is specific to amadori compounds.

2. Reaction specificity and substrate specificity FAOD of the present invention has a catalytic activity in the reaction below:

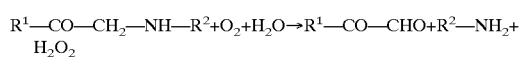

wherein $R^1$ is an aldose residue and $R^2$ is an amino acid, protein or peptide residue.

In the above reaction scheme, amadori compounds of the formula $R^1$—CO—$CH_2$—NH—$R^2$ wherein $R^1$ is —OH, —$(CH_2)_n$— or —$[CH(OH)]_n$—$CH_2OH$ (n is an integer of 0 to 6) and $R^2$ is —$CHR^3$—$[CONHR^3]_m$COOH ($R^3$ is a side chain residue of an α-amino acid and m is an integer of 1 to 480) are preferred as substrate. Among them, compounds wherein $R^3$ is a side chain residue of an amino acid selected from lysine, polylysine, valine, asparagine, etc., n is 5 to 6 and m is 55 or less are more preferred.

Substrate specificity of FAOD of the present invention is shown in Table 1 below.

TABLE 1

Substrate specificity of purified FAOD

| Substrate | Concentration | Specific activity (%) |
|---|---|---|
| $N^{\epsilon}$-Fructosyl $N^{\alpha}$-Z-lysine | 1.67 mM | 22.4 |
| Fructosyl valine | 1.67 mM | 100 |
| $N^{\epsilon}$-methyl-L-lysine | 1.67 mM | N.D.*1 |
| FHSA*2 | 0.17% | N.D. |
| Tryptic FHSA | 0.17% | 0.5 |
| Glycohemoglobin | 0.17% | N.D. |
| Tryptic glycohemoglobin | 0.17% | 0.2 |

[1]not detected
[2]fructosyl human serum albumin

As is apparent from Table 1, FAOD of the present invention is highly specific to both of FZL and fructosyl valine.

Examples of FAOD-producing strains of Penicillium and substrate specificity of FAODs are shown in Table 2 below.

TABLE 2

Substrate specificity of FAODs purified from strains of Penicillium grown in FZL browncolored medium

| Accession Number | Strain | Specific activity ($10^{-2}$ U/mg protein) | |
| | | Fructosyl $N^{\alpha}$-Z-lysine | Fructosyl valine |
|---|---|---|---|
| FERM BP-5475 | *Penicillium.janthinellum* S-3413 | 3.0 | 17.3 |
| IFO 4651 | janthinellum | 0.3 | 0.5 |
| IFO 6581 | janthinellum | N.D.[1] | 0.2 |
| IFO 7905 | janthinellum | 0.3 | 0.5 |

TABLE 2-continued

Substrate specificity of FAODs purified from strains of
Penicillium grown in FZL browncolored medium

| Accession Number | Strain | Specific activity (10⁻² U/mg protein) | |
|---|---|---|---|
| | | Fructosyl $N^\alpha$-Z-lysine | Fructosyl valine |
| IFO 5748 | *oxalicum* | 3.0 | 16.2 |
| IFO 7994 | *javanicum* | 2.8 | 12.0 |
| IFO 4897 | *chrysogenum* | 1.8 | 11.3 |
| IFO 5337 | *cyaneum* | 6.1 | 21.9 |

As is apparent from Table 2, FAODs of the present invention are more active on fructosyl valine compared to fructosyl lysine, which indicates that the said FAOD is useful for analysis of glycated hemoglobin.

3. pH and Temperature conditions

Determination of pH condition

The pH condition was determined by adding FAOD to a mixture of 0.1M acetic acid (Ac), potassium phosphate buffer (K—P), Tris-HCl buffer or glycine(Gly)-NaOH buffer (pH 4.0 to 11.0), incubating for 10 minutes at 25° C., and measuring the activity of FAOD under a normal condition (25° C., pH 8.0).

FAOD of the present invention, when evaluated according to the method above, is stable in the pH range of about 4.0 to 11.0, preferably pH 6.0 to 9.0. The optimal pH is about pH 7.5 (see, FIG. 2).

Determination of temperature condition

The temperature condition was determined by adding FAOD to a mixture of 50 mM potassium phosphate buffer (pH 7.5) at temperature ranging from 15° to 60° C., incubating the mixture under the same condition for 10 minutes and measuring the activity of FAOD under a normal condition.

FAOD of the present invention is stable at temperature range of 15° to 50° C., preferably 15° to 45° C., more preferably about 15° C. The enzyme reaction proceeds efficiently at 15° to 45° C., preferably 15° to 40° C., more preferably about 25° C. (see, FIG. 3).

4. Evaluation of titer

Titration was carried out as follows (1) Method utilizing calorimetric determination of generated hydrogen peroxide A. Measurement of generation rate A 100 mM fructosyl valine (hereinafter, referred to as FV) solution was prepared by dissolving previously-obtained FV in distilled water. To 100 μl of 45 mM 4-aminoantipyrine, 100 μl of 60 U/ml peroxidase, 100 μl of 60 mM phenol, 1 ml of 0.1M Tris-HCl buffer (pH 8.0) and 50 μl of enzyme solution was added distilled water to total volume of 2.95 ml. The mixture was equilibrated at 25° C. and 50 μl of 100 mM FV solution was added thereto. Then, the time course of absorbance at 505 nm was measured. The amount (μmole) of hydrogen peroxide generated per minute was calculated on the basis of molar absorptivity ($5.16 \times 10^3 M^{-1} cm^{-1}$) of quinone pigment produced. The resultant numerical value was taken as a unit(U) of enzyme activity.

B. End point method

According to the same manner as that described in the method A above, a solution was prepared and a substrate solution was added thereto. After 30-minute-incubation at 30° C., absorbance at 505 nm was measured. The enzyme activity was evaluated on the basis of the amount of hydrogen peroxide generated referring to a calibration curve previously obtained using a standard hydrogen peroxide solution.

(2) Method of determination of oxygen absorption due to enzyme reaction

To a mixture of 1 ml of 0.1M Tris-HCl buffer (pH 8.0) and 50 μl of an enzyme solution was added distilled water to obtain a solution of a total volume of 3.0 ml. The resulting solution was charged in a cell of an oxygen electrode manufactured by Lank Brothers Co. The solution was stirred at 25° C. to allow the dissolved oxygen to be equilibrated under the temperature and 100 μl of 50 mM FV was added thereto. Then, the oxygen absorption was continuously measured on a recorder to obtain an initial rate. The amount of oxygen absorbed for one minute was determined on the basis of a calibration curve, which was taken as an enzyme unit.

5. Inhibition, activation and stabilization of enzyme (1) Effect of metal

To an enzyme solution was added a solution containing a metal ion to be tested at a final concentration of 1 mM in 0.1M Tris-HCl buffer (pH 8.0). After 5-minute-incubation at 30° C., the enzyme activity was evaluated. The results are shown in Table 3 below.

TABLE 3

Effect of metal ion on the activity of FAOD
from *P. janthinellum* S-3413

| Metal (1 mM) | Specific activity (%) |
|---|---|
| None | 100 |
| LiCl | 88 |
| KCl | 103 |
| NaCl | 100 |
| RbCl | 105 |
| CsCl | 103 |
| $MgCl_2$ | 103 |
| $CaCl_2$ | 74 |
| $MnCl_2$ | 144 |
| $FeSO_4$ | 114 |
| $CoSO_4$ | 13 |
| $CuCl_2$ | 51 |
| $ZnSO_4$ | 5.8 |
| $AgNO_3$ | 5.7 |
| $BaCl_2$ | 66 |
| $HgCl_2$ | 2.1 |
| $FeCl_3$ | 100 |

As is apparent from Table 3, the activity of FAOD of the present invention seems to be inhibited by copper and barium ions and is strongly inhibited by cobalt, zinc, silver and mercury ions.

(2) Effect of various inhibitors

The inhibitory effect of various substances was tested in a manner substantially analogous to that described in (1) above. In the present test, the final concentration of parachloro mercuric benzoate (PCMB) is 0.1 mM while that of others 1 mM. The results are shown in Table 4. The stabilization effect was examined by dialyzing the purified FAOD overnight against 50 mM potassium phosphate buffer (pH 7.5) containing 0.1 mM dithiothreitol (DTT) and measuring the enzyme activity.

TABLE 4

Effect of various inhibitors on activity of FAOD

| Reagent (1 mM) | Specific activity (%) |
|---|---|
| None | 100 |
| PCMB*¹ | 0.69 |

TABLE 4-continued

Effect of various inhibitors on activity of FAOD

| Reagent (1 mM) | Specific activity (%) |
|---|---|
| DTNB*[2] | 13 |
| Iodoacetic acid | 102 |
| Sodium azide | 118 |
| α,α'-Dipyridyl | 105 |
| O-Phenanthroline | 111 |

TABLE 4-continued

Effect of various inhibitors on activity of FAOD

| Reagent (1 mM) | Specific activity (%) |
|---|---|
| Semicarbazide | 103 |
| Phenylhydrazine | 0.17 |
| Hydrazine | 12 |
| Hydroxylamine | 18 |
| Deprenyl | 107 |
| Aminoguanidine | 63 |
| EDTA*[3] | 109 |

*[1]PCMB, parachloro mercuric benzoate.
*[2]DTNB, 5,5'-Dithiobis(2-nitrobenzoic acid).
*[3]EDTA, ethylenediaminetetraacetic acid.

As is apparent from Table 4, the activity of FAOD is strongly inhibited by PCMB, DTNB, hydrazine, phenylhydrazine and hydroxylamine, indicating that SH and/or carbonyl group may plays an important role in the enzyme reaction.

The enzyme is stabilized by dithiothreitol (DTT), and preferable solvent for the preservation is 50 mM potassium phosphate buffer (pH 7.5) containing 0.1 mM DTT.

6. Molecular weight

Molecular weight, when determined by gel filtration on Superdex 200 pg, is about 38,700 (38.7 kD). (see, FIG. 4)

SDS-PAGE (sodium dodecyl sulfate polyacrylamide gel electrophoresis) was conducted according to the Davis's method using 10% gel at 40 mA for 3 hours and staining proteins with Coomassie brilliant blue G-250. The molecular weight of a subunit of FAOD, when determined on SDS-PAGE using calibration curve obtained by electrophoresing standard proteins including phosphorylase B, bovine serum albumin, ovalbumin, carbonic anhydrase and soybean trypsin inhibitor in the same manner, is about 48,700 (48.7 kDa). (see, FIG. 5) This indicates that the FAOD of the present invention is a monomer.

7. Comparison with known enzymes

FAOD of the present invention was compared with known fructosyl amino acid oxidases derived from various microorganisms.

TABLE 5

Comparison of Fructosyl Amino Acid Oxdases Derived from Various Microorganisms

| Microorganism | Penicillium jathinellum S-3413 | Corynebacterium sp.[1] | Aspergillus sp.[2] |
|---|---|---|---|
| Molecular weight | | | |
| (gel filtration) | 38,700 | 88,000 | 83,000 |
| (SDS-PAGE) | 48,700 | 44,000 | 43,000 |
| Coenzyme | Covalently-bonded FAD | Noncovalently-bonded FAD | Noncovalently-bonded FAD |
| Substrate specificity (U/mg Protein) | | | |
| (Fructosyl lysine) | 3.0[3] | N.D.[4] | 11.28[4] |
| (Fructosyl valine) | 17.3 | 7.09 | 59.8 |
| Optimum pH | 7.5 | 8.3 | 7.7 |
| Optimum temperature (°C.) | 25 | 40 | 40 |
| Inactivation by SH reagent | Inactivated | not inactivated | Inactivated |

[1]T. Horiuchi et al., Agric. Biol. Chem., 53 (1), 103–110 (1989)
[2]T. Horiuchi et al., Agric. Biol. Chem., 55 (2), 333–338 (1991)
[3]Specific activity to fructosyl $N^\alpha$-Z-lysine
[4]Specific activity to $N^\epsilon$-D-fructosyl $N^\alpha$-formyllysine As is apparent from Table 5, the following differences can be noted between FAOD of the present invention and others derived from two strains.

(1) Molecular weight: FAOD of the present invention is a monomer, while the others dimmers.

(2) Coenzyme: FAOD of the present invention requires covalently-bonded FAD, while the others noncovalently-bonded FAD.

(3) Optimal pH, optimal temperature, and inhibition by SH reagents: the data indicate that FAOD of the present invention is distinguishable from other enzymes.

The difference between FAOD of the present invention and the fructosyl amino acid deglycase derived from Penicillium (Japanese Laid-Open Patent Publication No. 4-4874) is shown below.

(1) Substrate specificity: the fructosyl amino acid deglycase is active on fructosyl lysine and fructosyl alanine, while FAOD of the present invention is active on fructosyl lysine and fructosyl valine with preference in fructosyl valine.

(2) Induction specificity: the fructosyl amino acid deglycase can be produced in a medium free from fructosyl amino acid, while FAOD of the present invention is induced by growing a strain of Penicillium in a medium containing fructosyl lysine.

(3) Preparation process: FAOD of the present invention is efficiently prepared by cultivating a strain of Penicillium in "brown-colored medium".

As discussed above, FAOD of the present invention is useful in an assay of amadori compounds. Accordingly, the present invention provides an assay of an amadori compound in a sample, which comprises bringing the sample containing an amadori compound into contact with FAOD of the present invention and determining the amount of oxygen consumed or that of hydrogen peroxide produced. The assay of the present invention is carried out on the basis of the measurement of the amount of glycated protein and/or glycation rate, or the determination of fructosyl amine in a sample derived from a living body.

The enzyme activity of FAOD is evaluated by the following reaction scheme:

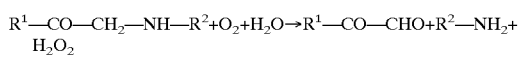

wherein $R^1$ is an aldose residue and $R^2$ is an amino acid, protein or peptide residue.

As a sample solution to be tested, there can be used any solutions containing an amadori compound(s), for example, those derived from food products such as soy sauce, etc. as well as a living body such as blood (e.g. whole blood, plasma or serum), urine, or the like.

FAOD of the present invention is reacted with a sample containing an amadori compound in a suitable buffer. Although the suitable pH and temperature of the reaction mixture may vary depending on the enzyme to be used and the sample to be tested, they can be within the range defined above, that is, at pH from 6.0 to 9.0, preferably 7.5 and at temperature from 15° to 45° C., preferably 15° to 40° C. As buffer, potassium phosphate buffer can be used.

The amount of FAOD to be used in an assay is normally 0.1 unit/ml or more, preferably 1 to 100 units/ml in the case of end point method.

For purposes of the present invention, the determination of amadori compounds can be carried out by any one of known assays shown below.

(1) Determination based on the amount of hydrogen peroxide generated

The amount of amadori compounds in a sample can be estimated from the amount of hydrogen peroxide produced according to a method for determination of hydrogen peroxide such as calorimetric method or a method utilizing a hydrogen peroxide electrode. The amount of amadori compound in a sample is then estimated on the basis of a calibration curve regarding the relation between the amount of hydrogen peroxide and that of amadori compounds. Specifically, the estimation can be conducted in a manner similar to that described in "4. Evaluation of titer", except that the amount of FAOD is 1 unit/ml and that a sample to be tested is diluted before the measurement of hydrogen peroxide produced.

As the color-developing system for hydrogen peroxide, there can be used any systems which develop color due to oxidative condensation between a chromogen such as phenol and a coupler such as 4-aminoantipyrine, 3-methyl-2-benzothiazolinone hydrazone in the presence of peroxidase. Examples of chromogen include phenolic derivatives, aniline derivatives and toluidine derivatives, for example, N-ethyl-N-(2-hydroxy-3-sulfopropyl)-m-toluidine, N, N-dimethylaniline, N,N-diethylaniline, 2,4- dichlorophenol, N-ethyl-N-(2-hydroxy-3-sulfopropyl)-3,5-dimethoxyaniline, N-ethyl-N-(3-sulfopropyl)-3,5-dimethylaniline, and N-ethyl-N-(2-hydroxy-3-sulfopropyl)-3,5-dimethylaniline. A leuco-type color-developing agent which develops color upon oxidation in the presence of peroxidase is also available. Such "leuco-type color developing agents" are known in the art and examples thereof include o-dianisidine, o-tolidine, 3,3-diaminobenzidine, 3,3, 5,5-tetramethylbenzidine, N-(carboxymethylaminocarbonyl)-4,4-bis(dimethylamino)-biphenylamine, 10-(carboxymethylaminocarbonyl)-3,7-bis (dimethylamino)phenothiazine and the like.

(2) Determination on the basis of the amount of oxygen consumed

Amadori compound in a sample can be estimated from the amount of oxygen consumed which is calculated by subtracting the amount of oxygen at the completion of reaction from the one at the beginning of reaction using a calibration curve concerning the relation of the amount of oxygen consumed and that of amadori compounds. Specifically, it can be conducted in a manner similar to the titration described in "4. Evaluation of titer" above, except that the amount of FAOD is 1 unit/ml and that a sample to be added is previously diluted appropriately before the measurement of oxygen consumed.

According to the assay of the present invention, a sample solution can be used as it is, but it may be preferred in a certain occasion that the sample is pre-treated so as to liberate lysine and/or valine residue to which sugar is bound in a glycated protein.

For such a purpose, the sample is treated with a protease (enzymic method) or a chemical substance such as hydrochloric acid, etc. (chemical method). The enzymic method is preferred. In such a case, proteases of endo- and exo-type known in the art can be used in the process of the present invention. Examples of endo-type protease include trypsin, α-chymotrypsin, subtilisin, proteinase K, papain, cathepsin B, pepsin, thermolysin, protease XIV, lysylendopeptidase, proleser and bromelain F. Examples of exo-type protease include aminopeptidase and carboxypeptidase. The method of the enzyme treatment is also known and, for example, the trypsin treatment can be conducted as described in Examples below.

As mentioned above, FAOD of the present invention is specific to fructosyl valine and therefore useful in the assay of glycated hemoglobin. In another aspect, FAOD of the present invention is specific to fructosyl lysine contained in glycated protein and is useful in the diagnosis and control of conditions of diabetes, which comprise measuring glycated proteins in blood sample.

When blood (e.g. whole blood, plasma or serum) is to be assayed, a blood sample derived from a living body can be used as it is or after pre-treatment such as dialysis, etc.

Further, enzymes (e.g. FAOD, peroxidase, etc.) used in the process of the present invention can be used in a liquid state or after immobilizing to suitable solid supports. For example, a column packed with enzyme immobilized onto beads can be used to obtain an automated device for assay of glycated protein, or the like, which device must improve the efficiency of a routine assay such as clinical examination where a lot of specimens must be tested in accuracy and rapidity. The immobilized enzyme has another advantage in view of economical efficiency because it can be used repeatedly.

Furthermore, it is possible to provide a kit by combining an enzyme(s) with a color-developing reagent(s) in an appropriate manner. Such a kit is useful for both of clinical assay and food analysis of amadori compounds.

The immobilization of the enzyme can be conducted by a method known in the art. For example, it is conducted by a carrier bonding method, cross-linkage method, inclusion method, complexing method, and the like. Examples of carriers include polymer gel, microcapsule, agarose, alginic acid, carrageenan, and the like. The enzyme can be bound to a carrier through covalent bond, ionic bond, physical absorption, biochemical affinity, etc. according to a method known in the art.

When using immobilized enzyme, the assay may be carried out in flow or batch system. As described above, the immobilized enzyme is particularly useful for a routine assay (clinical examination) of glycated proteins in blood samples. When the clinical examination is directed to the diagnosis of diabetes, the result as criterion for diagnosis of diabetes is expressed in concentration of glycated protein or glycation rate which is the ratio of the concentration of glycated protein to that of whole protein in the sample or the amount of fructosyl amine. The whole protein concentration can be determined in a conventional manner, for example, through the measurement of absorbance at 280 nm, Bradford method, Lowry method, bullet method, natural fluorescence of albumin, or the absorbance of hemoglobin.

The present invention also provides a reagent or a kit used in an assay of amadori compounds, which comprises FAOD of the present invention and a buffer whose pH is preferably 6.0 to 9.0, more preferably 7.5. When FAOD is immobilized, the solid support can be selected from a polymer gel and the like, and alginic acid is preferred.

In the case of end point assay, the reagent usually contains 1 to 100 units/ml of FAOD for each sample, and potassium phosphate buffer (pH 7.5) as a buffer.

When amadori compounds are assayed on the basis of generated hydrogen peroxide, any of the color-developing systems which develop color due to oxidative condensation, leuco-type color-developing agents and the like described in "(1) Determination based on the amount of hydrogen peroxide generated" above can be used.

The reagent used in an assay of amadori compound of the present invention may be combined with a suitable color-developing agent together with a color criterion or a standard substance to give a kit which is useful for a preliminary diagnosis or examination.

The reagent or the kit described above is used for measurement of the amount of glycated protein and/or glycation rate or the determination of fructosyl amine in a sample derived from a living body.

As is described above, FAOD of the present invention is specific to both of fructosyl lysine and fructosyl valine and therefore is useful in the development of novel clinical assays and food analyses, and thereby contributing to the diagnosis of diabetes and quality control of food products. In particular, it is expected to be useful in a diagnosis of diabetes where the amount of glycated protein and/or glycation rate or the amount of fructosyl amine in blood as an index for diagnosis or control of conditions of diabetes. It is now possible to determine glycated proteins accurately and efficiently by means of assay using a reagent of the present invention for determination of amadori compounds, which facilitates the diagnosis or control of conditions of diabetes.

The following Examples further illustrate the present invention in detail but are not to be construed to limit the scope thereof.

Example 1 Fermentation of *P. janthinelum* S-3413 and Purification of FAOD

1) Fermentation

*P. janthinellum* S-3413 (FERM BP-5475) was inoculated into a medium (pH 6.0, 10 L) containing 0.5% FZL, 1.0% glucose, 0.1% $K_2HPO_4$, 0.1% $NaH_2PO_4$, 0.05% $MgSO_4$, 0.01% $CaCl_2$ and 0.2% yeast extract, and grown at 28° C. for 36 hours with aeration (2 L/min) and stirring (500 rpm) using a jar fermentor. The culture was filtered to harvest mycelia.

2) Preparation of Crude Extract

A portion of mycelia (410 g, wet weight) was suspended in 0.1M potassium phosphate buffer (pH 7.5, 800 ml) containing 0.1 mM DTT and ground with Dino-Mill. The ground mixture was centrifuged at 9,500 rpm for 20 minutes to obtain the supernatant (cell-free extract) as a crude extract, which was then subjected to purification.

3) Purification

To the crude extract was added ammonium sulfate to 40% saturation and the mixture was centrifuged at 12,000 rpm, for 10 minutes. To the supernatant was added ammonium sulfate to 75% saturation, stirred and centrifuged at 12,000 rpm for 10 minutes.

The precipitates were dissolved in 50 mM potassium phosphate buffer (pH 7.5) containing 0.1 mM DTT (hereinafter, referred to as "buffer A")and the solution was dialyzed overnight against the buffer A while changing the dialysis solvent twice. The resultant enzyme solution was applied to DEAE-Sephacel column (4.2×26 cm) equilibrated with the buffer A. Activity was observed in the washing fractions with the buffer A, which were collected and subjected to fractionation with ammonium sulfate ranging from 0 to 55% saturation. The resultant substance was adsorbed onto phenyl-Sepharose 6FF (Low substitute) column (HR 10/10) equilibrated with the buffer A containing 25% ammonium sulfate. After washing with the same buffer, the column was eluted with a linear gradient of 25 to 0% saturation of ammonium sulfate. The active fractions were pooled, concentrated with ammonium sulfate, and subjected to gel filtration on Superdex 200 pg column equilibrated with 0.2M potassium phosphate buffer (pH 7.5) containing 0.1M DTT to give an purified enzyme preparation of 70 to 100 units.

Figure 1:
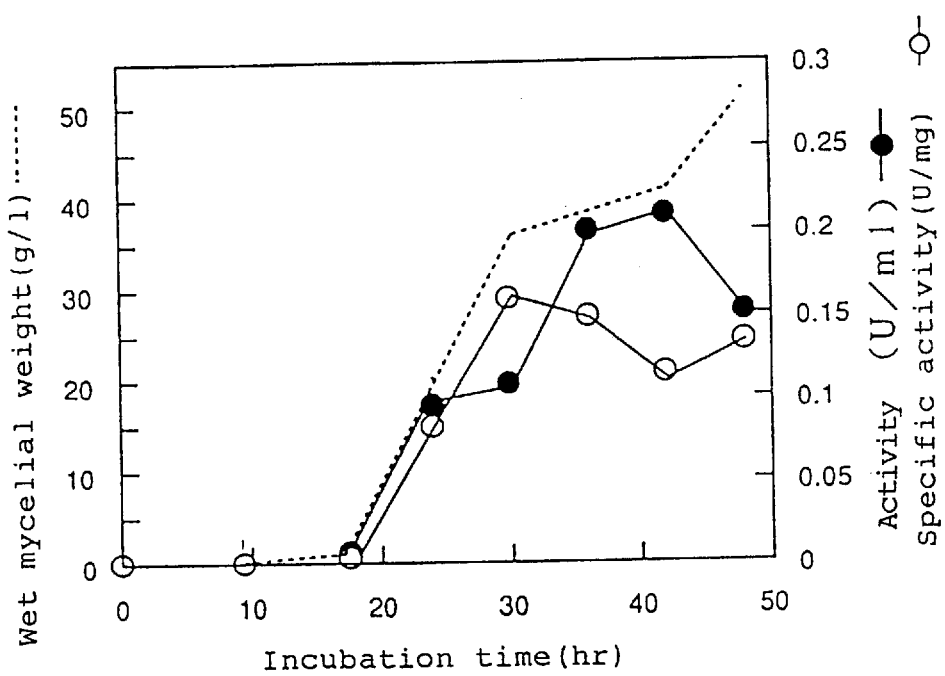
FIG. 1 is a graph showing a relation between the cultivation time and the amount of FAOD produced in a culture medium by *P. janthinellum* S-3414.
Figure 2:
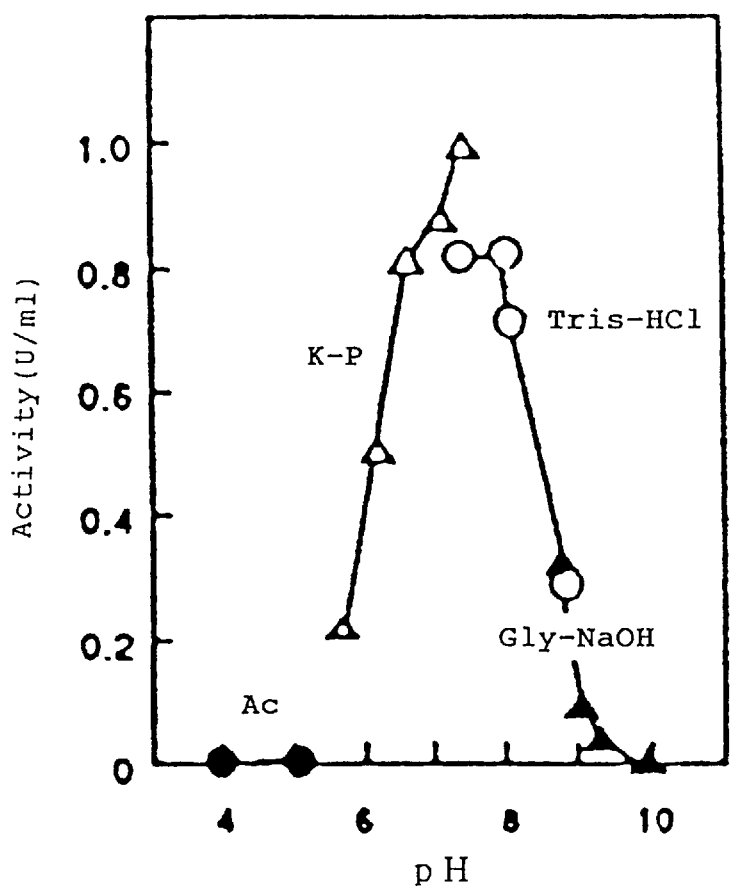
FIG. 2 is a graph showing a relation between the optimum pH and the activity of FAOD in a solvent.
Figure 3:
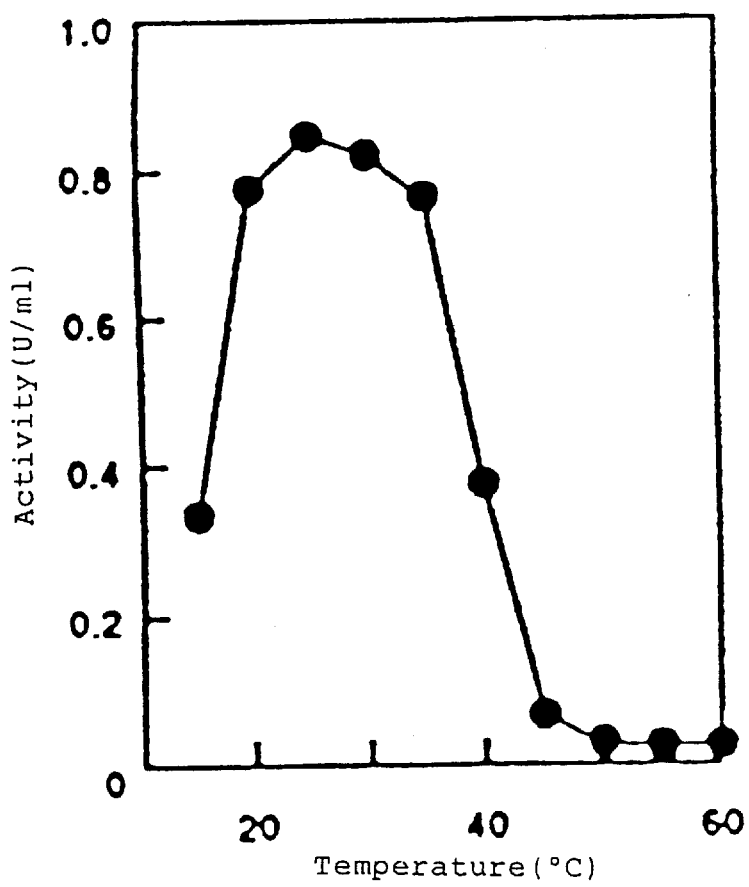
FIG. 3 is a graph showing a relation between the optimum temperature and the activity of FAOD in a solvent.
Figure 4:
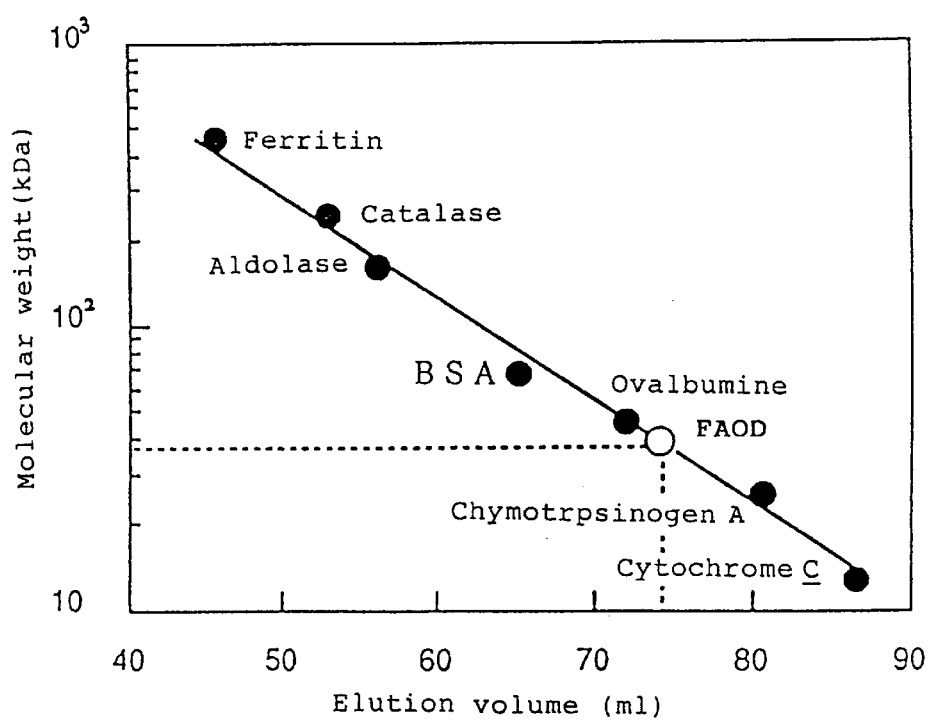
FIG. 4 is a graph showing the molecular weight of FAOD measured by gel filtration on Superdex 200 pg.

The gel filtration with Superdex 200 pg revealed that the molecular weight is about 38,700 (38.7 kDa) on the basis of calibration curve as shown in FIG. 4.

Figure 5:
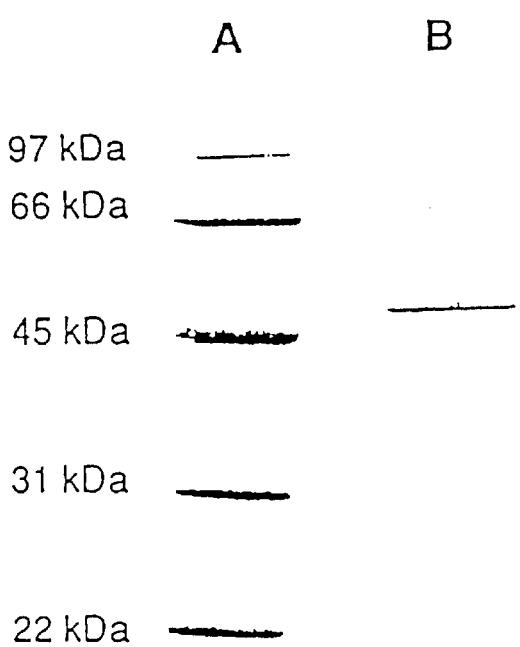
FIG. 5 is a photograph showing the migration pattern of purified FAOD from *P. janthinellum* S-3413 on SDS-PAGE.

The purified enzyme was used for determination of molecular weight by SDS-PAGE according to the Davis's method using 10% gel at 40 mA for 3 hours and staining proteins with Coomassie brilliant blue G-250. Molecular weight was estimated using a calibration curve prepared by electrophoresing standard proteins including phosphorylase B, bovine serum albumin (BSA), ovalbumin, carbonic anhydrase and soybean trypsin inhibitor in the same manner. SDS-PAGE revealed that the molecular weight of the purified enzyme subunit is about 48,700 (48.7 kDa) (see, FIG. 5).

Figure 6:
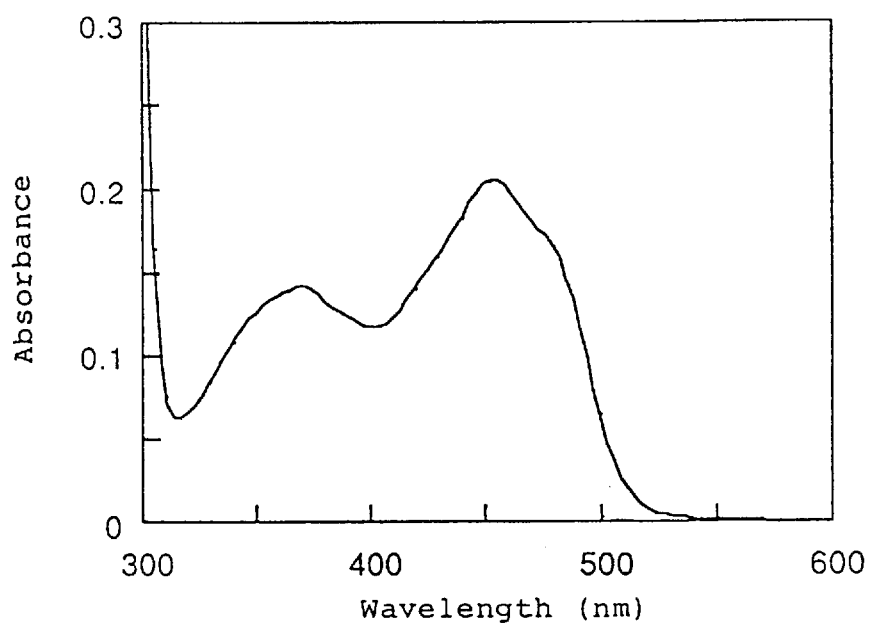
FIG. 6 shows absorption spectrum of a purified FAOD from *P. janthinelum* S-3413.

UV absorption spectrum of the purified enzyme is shown in FIG. 6, which indicates that the enzyme is a flavin enzyme.

Furthermore, FAOD prepared in Example 1 showed the same values or physicochemical properties in connection with enzyme activity, pH and temperature stability, effect of metal and inhibitors, etc., as those described above.

Example 2 Determination of Glycated Hemoglobin

1) Preparation of Sample

A sample solution as substrate of FAOD was prepared as follows. To a solution of 0 to 15 mg of glycohemoglobin control E (Sigma) in 100 µl of distilled water was added 1 ml of hydrochloric acid in acetone (1N HCl/acetone, 1:100). The mixture was centrifuged at 12000 rpm for ten minutes, and the precipitates were washed with 500 µl of diethyl ether and concentrated to dryness under vacuum. To the residue was added 100 µl of 8M urea. The resultant mixture was heated in boiling water for 20 minutes, cooled, mixed with 300 µl of 5.4 U/ml trypsin, incubated at 37° C. for 3 hours, and heated in boiling water for 5 minutes to obtain a sample solution.

2) Determination of Activity

| | |
|---|---|
| 3 mM N-(carboxymethylaminocarbonyl)-4,4-bis(dimethylamino)biphenylamine solution | 30 µl |
| Peroxidase solution (60 units/ml) | 30 µl |
| 0.1M Tris-HCl buffer (pH 8.0) | 300 µl |
| FAOD solution (25 units/ml) | 5 µl |

FAOD solution (25 units/ml) was prepared by diluting the purified FAOD obtained in Example 1 with 0.1M potassium phosphate buffer (pH 7.5). After combining all the reagents listed above, the total volume was adjusted to 1 ml with distilled water to give an FAOD reaction mixture. To the FAOD reaction mixture was added a sample solution (150 µl) as substrate obtained in 1) above. The mixture was incubated at 30° C. and, 30 minutes later, the absorbance at 727 nm was measured to evaluate the relationships between the amount of glycated hemoglobin and absorbance.

3) Results

Figure 7:
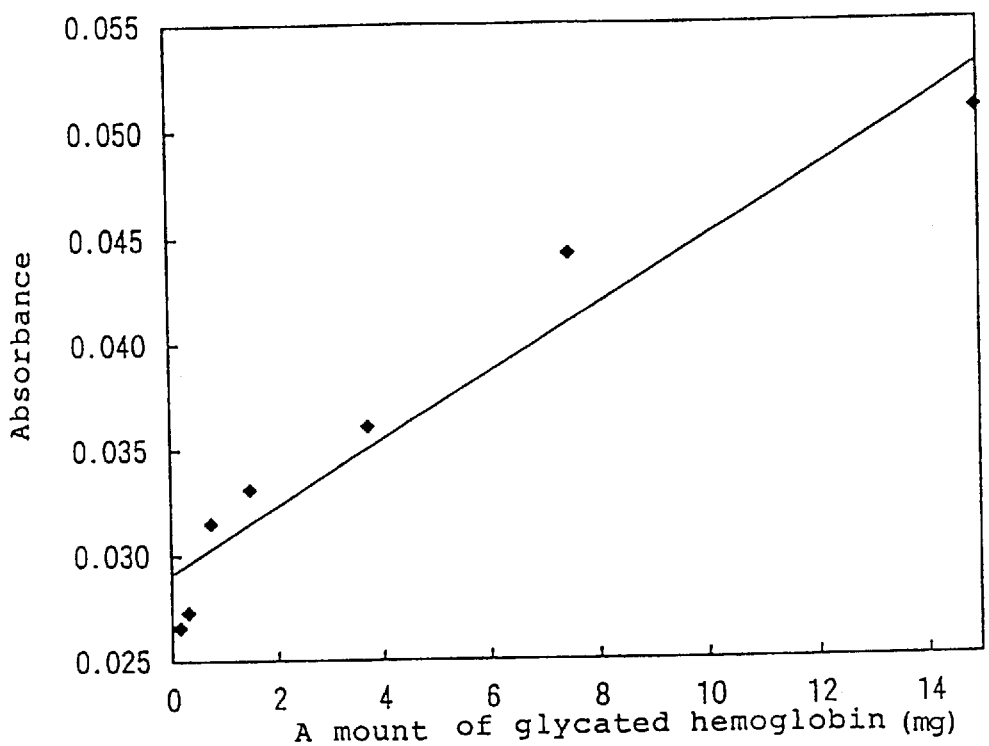
FIG. 7 is a graph showing the relation between amount of glycated hemoglobin and the amount of hydrogen peroxide produced due to FAOD action.

The results are shown in FIG. 7, wherein the ordinate indicates the absorbance at 727 nm corresponding to the amount of hydrogen peroxide generated and the abscissa indicates the amount of glycated hemoglobin. FIG. 7 shows that the amount of the glycated hemoglobin and the amount of hydrogen peroxide are correlated.

Example 3 Determination of Glycated Hemoglobin

1) Preparation of Sample

A sample solution as substrate of FAOD was prepared as follows. To a solution of 30 mg of glycohemoglobin control E (Sigma) in 200 µl of distilled water was added 1 ml of 570 mM Tris-HCl buffer (pH 8.8) containing 8M urea, 0.2% disodium EDTA and 40 µl of 2-mercaptoethanol and the mixture was allowed to stand for 2 hours under nitrogen atmosphere. After the addition of 400 µl of 1M sodium acetic iodide, the mixture was allowed to stand for 30 minutes, followed by further addition of 40 µl of 2-mercaptoethanol. The mixture was dialyzed against 0.1M ammonium hydrogen carbonate, mixed with 10 µl of 10 mg/ml TPCK-trypsin, incubated at 37° C. for 3 hours, and heated in boiling water for 5 minutes to obtain a sample solution.

2) Determination of Activity

| | |
|---|---|
| 3 mM N-(carboxymethylaminocarbonyl)-4,4-bis(dimethylamino)biphenylamine solution | 30 µl |
| Peroxidase solution (60 units/ml) | 30 µl |
| 0.1M Tris-HCl buffer (pH 8.0) | 300 µl |
| FAOD solution (25 units/ml) | 10 µl |
| Sample | 0 to 13.2 mg |

FAOD solution (25 units/ml) was prepared by diluting the purified FAOD obtained in Example 1 with 0.1M potassium phosphate buffer (pH 7.5). After combining all the reagents listed above, the total volume was adjusted to 900 µl with distilled water to obtain an FAOD reaction mixture. The FAOD reaction mixture was incubated at 30° C. and, 30 minutes later, the absorbance at 727 nm was measured to evaluate the relationships between the amount of glycated hemoglobin and absorbance.

3) Results

Figure 8:
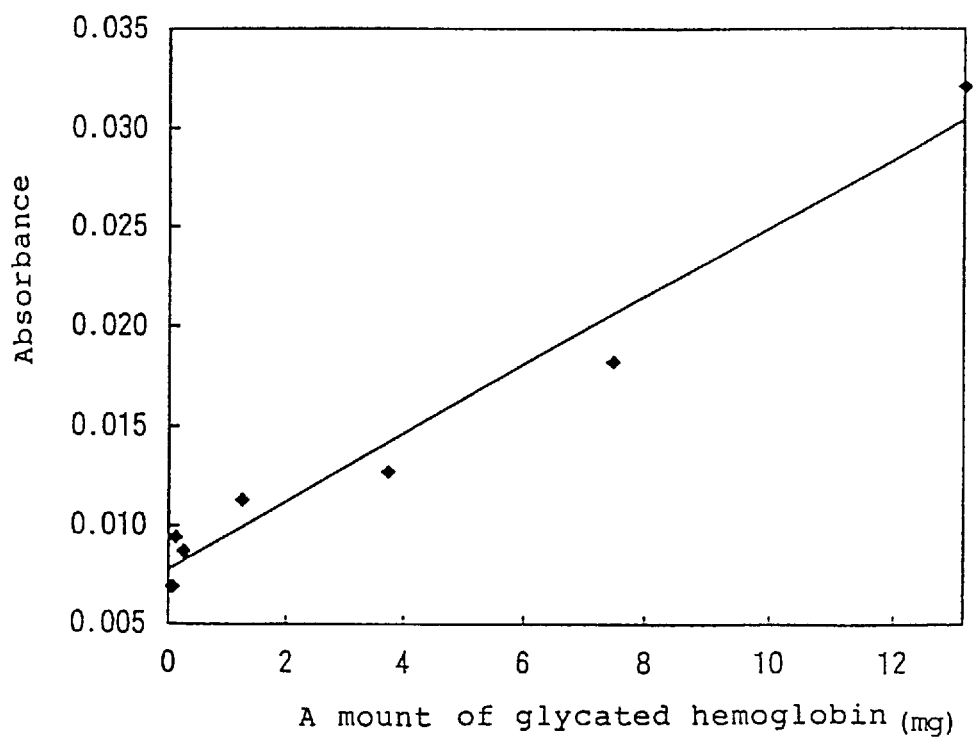
FIG. 8 is a graph showing the relation between amount of glycated hemoglobin and the amount of hydrogen peroxide produced due to FAOD action.

The results are shown in FIG. 8, wherein the ordinate indicates the absorbance at 727 nm corresponding to the amount of hydrogen peroxide generated and the abscissa indicates the amount of glycated hemoglobin. FIG. 8 shows that the amount of the glycated hemoglobin and the amount of hydrogen peroxide are correlated.

Example 4 Measurement of Hemoglobin Alc Level

1) Preparation of Sample

A sample solution as substrate was prepared as follows. Hemoglobin AO reagent (Sigma Co.) was dissolved in distilled water to give a 2.3 mM solution, which was fractionated using an automatic glycohemoglobin measuring device (Kyoto Daiichi Kagaku Co. Ltd.) Fractions each containing purified hemoglobin Alc and hemoglobin AO were collected. Sample solutions as substrate each having different hemoglobin Alc level ranging from 0% to 52.0% were prepared by mixing these fractions in various ratio.

2) Pre-treatment of Sample

A 200 µl mixture of 250 µg of a sample solution obtained in 1) above, 5 µl of 500 U/ml aminopeptidase and 15 µl of 1.0M Tris-HCl buffer (pH 8.0) in distilled water was incubated at 30° C. for 30 minutes. After addition of 200 µl of 10% trichloroacetic acid, the mixture was stirred, allowed to stand for 20 minutes at 0° C., and centrifuged at 12000 rpm for 10 minutes. The resultant supernatant was neutralized with about 40 µl of 5N NaOH.

3) Determination of Activity

| | |
|---|---|
| 3 mM N-(carboxymethylaminocarbonyl)-4,4-bis(dimethylamino)biphenylamine solution | 100 µl |
| Peroxidase solution (60 units/ml) | 100 µl |
| 0.1M Tris-HCl buffer (pH 8.0) | 1000 µl |
| FAOD solution (16 units/ml) | 15 µl |
| Sample | 0 to 13.2 mg |

FAOD solution (16 units/ml) was prepared by diluting the purified FAOD obtained in Example 1 with 0.1M potassium phosphate buffer (pH 7.5). After combining all the reagents listed above, the total volume was adjusted to 2.6 ml with distilled water to obtain an FAOD reaction mixture. The FAOD reaction mixture was incubated for 2 minutes at 30° C. After addition of 400 µl of a pre-treated substrate obtained in 2) above, the mixture was incubated for another 30 minutes and subjected to the measurement of absorbance at 727 to evaluate the relationships between the hemoglobin Alc level of a substrate and absorbance.

4) Results

Figure 9:
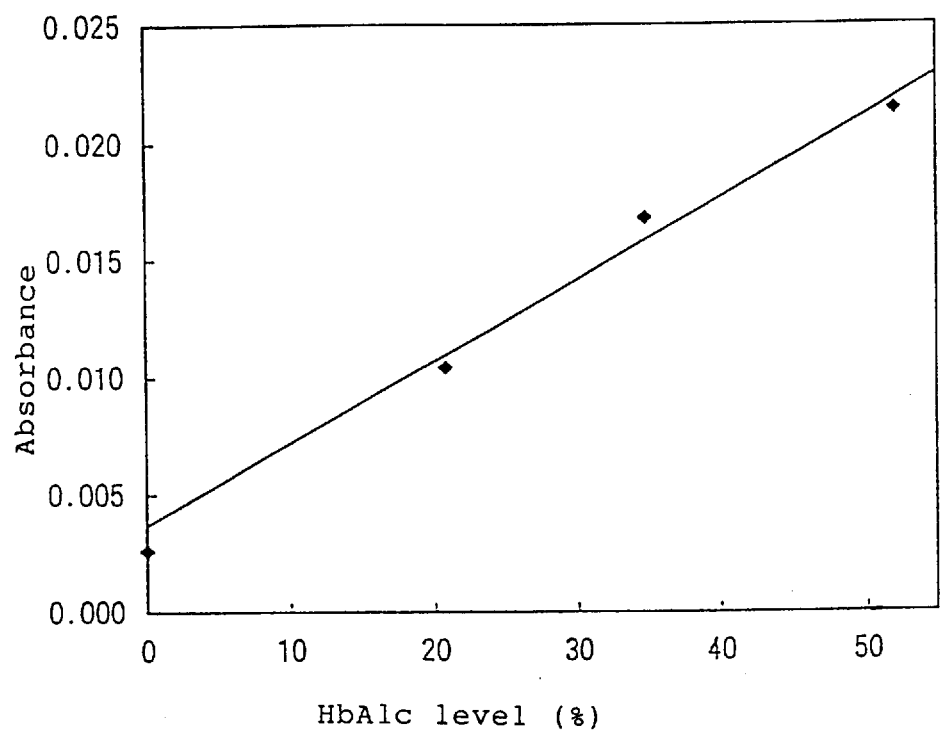
FIG. 9 is a graph showing the relation between hemoglobin Alc level and the amount of hydrogen peroxide produced due to FAOD action.

The results are shown in FIG. 9, wherein the ordinate indicates the absorbance at 727 nm corresponding to the amount of hydrogen peroxide generated and the abscissa indicates the hemoglobin Alc level. FIG. 9 shows that the hemoglobin Alc level and the amount of hydrogen peroxide are correlated.

What is claimed is:

1. An isolated fructosyl amino acid oxidase, which is produced by culturing a strain of Penicillium capable of producing a fructosyl amino acid oxidase in a fructosyl lysine-containing medium, and has physicochemical characteristics as follows:
   1) it catalyzes the oxidation of an amadori compound in the presence of oxygen to generate a-ketoaldehyde, amine derivatives and hydrogen peroxide;
   2) it is stable in the pH range of 4.0 to 11.0 with an optimal pH of 7.5;
   3) it is stable in the temperature range of about 15° to 50° C. with an optimal temperature of 25° C.; and
   4) the molecular weight is about 38,700 Da;
   5) it is more specific to fructosyl valine than to fructosyl lysine.

2. The fructosyl amino acid oxidase of claim 1, wherein the fructosyl lysine-containing medium contains fructosyl lysine and/or fructosyl $N^{\alpha}$-Z-lysine which can be obtained by autoclaving glucose together with lysine and/or $N^{\alpha}$-Z-lysine at 100° to 150° C. for 3 to 60 minutes.

3. The fructosyl amino acid oxidase of claim 1, which is active on fructosyl valine and/or fructosyl lysine.

4. The fructosyl amino acid oxidase of claim 1, wherein the strain of Penicillium is selected from the group consisting of *Penicillium janthinellum* FERM BP-5475, *Penicillium janthinellum* IFO No. 4651, 6581, 7905, *Penicillium oxalicum* IFO No. 5748, *Penicillium javanicum* IFO No. 7994, *Penicillium chrysogenum* IFO No. 4897 and *Penicillium cyaneum* IFO No. 5337.

5. A biologically pure culture of *Penicillium janthinellum* FERM BP-5475.

6. A process for producing a fructosyl amino acid oxidase of claim 1, which comprises culturing a strain of Penicillium capable of producing a fructosyl amino acid oxidase in a medium containing fructosyl lysine and/or fructosyl $N^{\alpha}$-Z-lysine and recovering fructosyl amino acid oxidase from the resulting culture.

7. An assay of an amadori compound in a sample containing amadori compounds, which comprises bringing the sample into contact with a fructosyl amino acid oxidase of claim 1 and determining the amount of oxygen consumed or the amount of hydrogen peroxide generated.

* * * * *